United States Patent
Keller et al.

(10) Patent No.: US 11,911,319 B2
(45) Date of Patent: Feb. 27, 2024

(54) PATIENT POSITIONING DEVICE AND MEDICAL WORKSTATION

(71) Applicant: KUKA Deutschland GmbH, Augsburg (DE)

(72) Inventors: Henrik Keller, Düsseldorf (DE); Dieter Schaab, Augsburg (DE)

(73) Assignee: KUKA Deutschland GmbH, Augsburg (DE)

( * ) Notice: Subject to any disclaimer, the term of this patent is extended or adjusted under 35 U.S.C. 154(b) by 221 days.

(21) Appl. No.: 17/422,082

(22) PCT Filed: Nov. 27, 2019

(86) PCT No.: PCT/EP2019/082647
§ 371 (c)(1),
(2) Date: Sep. 2, 2021

(87) PCT Pub. No.: WO2020/143955
PCT Pub. Date: Jul. 16, 2020

(65) Prior Publication Data
US 2022/0104984 A1  Apr. 7, 2022

(30) Foreign Application Priority Data
Jan. 9, 2019 (DE) .................... 10 2019 200 187.4

(51) Int. Cl.
*A61G 13/04* (2006.01)
(52) U.S. Cl.
CPC .................................. *A61G 13/04* (2013.01)
(58) Field of Classification Search
CPC ...... A61G 13/04; A61G 13/02; A61B 6/0407; A61B 6/0487; B25J 5/02; B25J 9/046;
(Continued)

(56) References Cited

U.S. PATENT DOCUMENTS 5,293,107 A   3/1994  Akeel
5,523,662 A *  6/1996  Goldenberg .......... B25J 17/025
                                                       901/23
(Continued)

FOREIGN PATENT DOCUMENTS

DE   102016210496 A1   12/2017
DE   102016211538 A1   12/2017
(Continued)

OTHER PUBLICATIONS

European Patent Office; Search Report in related International Patent Application No. PCT/EP2019/082647 dated Mar. 6, 2020; 5 pages.
(Continued)

*Primary Examiner* — Myles A Throop
(74) *Attorney, Agent, or Firm* — Dorton & Willis, LLP (57) ABSTRACT

A patient-positioning device includes a first link designed as a base frame for fastening the patient-positioning device on a support surface, a second link mounted on the first link for rotation about a first axis of rotation by a first joint, and a third link mounted on the second link for rotation about a second axis of rotation by a second joint. The third link is arranged on the second link by the second joint in such a way that, with a floor mounting of the first link, the third link is arranged below the second link by the second joint in order to suspend the third link on the second link in an overhead arrangement by means of the second joint. The third link is mounted so as to be rotatable under the second link by the second joint.

14 Claims, 5 Drawing Sheets

(58) Field of Classification Search
CPC ...... B25J 9/102; B25J 18/005; B25J 19/0029; B25J 9/042
See application file for complete search history.

(56) References Cited

U.S. PATENT DOCUMENTS

| | | | |
|---|---|---|---|
| 6,068,442 | A | 5/2000 | Flemmer et al. |
| 2005/0234327 | A1 | 10/2005 | Saracen et al. |
| 2009/0114052 | A1* | 5/2009 | Haniya ............... B25J 9/06 901/23 |
| 2012/0174317 | A1* | 7/2012 | Saracen ............ A61B 6/4458 901/29 |
| 2019/0255359 | A1* | 8/2019 | Benali ............... A61N 5/1069 |
| 2019/0298276 | A1* | 10/2019 | Pinault ............. A61B 6/4458 |

FOREIGN PATENT DOCUMENTS

| | | | |
|---|---|---|---|
| GB | 2481249 | A | 12/2011 |
| JP | H06285779 | A | 10/1994 |
| WO | 2009005556 | A1 | 1/2009 |
| WO | 2017216073 | A1 | 12/2017 |
| WO | 2017216075 | A1 | 12/2017 |
| WO | 2017216077 | A1 | 12/2017 |

OTHER PUBLICATIONS

Chinese Patent Office; Office Action in related Chinese Patent Application No. 201980093822.X dated Jul. 12, 2023; 8 pages.

* cited by examiner

PATIENT POSITIONING DEVICE AND MEDICAL WORKSTATION

CROSS-REFERENCE TO RELATED APPLICATIONS

This application is a national phase application under 35 U.S.C. § 371 of International Patent Application No. PCT/EP2019/082647, filed Nov. 27, 2019 (pending), which claims the benefit of priority to German Patent Application No. DE 10 2019 200 187.4, filed Jan. 9, 2019, the disclosures of which are incorporated by reference herein in their entirety.

TECHNICAL FIELD

The invention relates to a patient-positioning device, and an associated medical workstation having such a patient-positioning device.

BACKGROUND

DE 10 2016 210 496 A1 discloses a patient-positioning device, comprising a patient table comprising a lying surface and a robotic arm which has a plurality of links arranged one behind the other, rotatably mounted with respect to axes and a fastening device to which the patient table is fastened, wherein the links of the robotic arm comprise a robotic hand which comprises hand links and the fastening device, and wherein a first link of the links of the robotic arm is mounted in the region of one of its two ends so as to rotate with respect to a vertically extending axis, a second link of the links of the robotic arm is mounted in the region of one of its two ends in the region of the other end of the first link so as to rotate with respect an axis extending horizontally relative to the first link, and the robotic hand is mounted in the region of the other end of the second link so as to rotate with respect to a further axis extending horizontally relative to the second link, wherein the horizontally extending axis is aligned at a distance parallel to the further horizontally extending axis.

DE 10 2016 211 538 A1 discloses a robot, for example for patient-positioning, comprising a robotic arm having a plurality of robot links which are connected to one another via axis units, wherein the axis units each define at least one movement axis of the robotic arm, wherein the robotic arm comprises a first end region, which allows it to be arranged in a surrounding region of the robot, and a second end region on which an end effector can be arranged, wherein a first axis unit downstream of the first end region defines a first axis of rotation of the robotic arm, and wherein the robotic arm can be arranged in the surrounding region by means of the first end region in such a way that the first axis of rotation is at an oblique angle to the surrounding region.

WO 2017/216075 A1 discloses a patient-positioning device, comprising:
a patient table that comprises a lying surface for a person,
a robotic arm with eight links and seven joints, which are arranged alternately in series in a kinematic chain of the robotic arm,
wherein the first link in the kinematic chain of the robotic arm forms a base frame for fastening the robotic arm on a support surface, and the eighth link in the kinematic chain of the robotic arm forms a mounting flange of a robotic hand of the robotic arm to which the patient table is fastened,
the second link is mounted on the first link so as to be rotatable about a first vertical axis of rotation by means of the first joint,
the third link is mounted on the second link so as to be rotatable about a second, vertical axis of rotation by means of the second joint,
the fourth link is mounted on the third link so as to be rotatable about a third, vertical axis of rotation by means of the third joint,
the fifth link is mounted on the fourth link so as to be rotatable about a fourth, horizontal axis of rotation by means of the fourth joint,
and the robotic hand of the robotic arm is attached to the fifth link, which robotic hand comprises the sixth link, the seventh link and the eighth link, as well as the fifth joint, the sixth joint and the seventh joint of the robotic arm.

WO 2017/216077 A1 discloses a patient-positioning device, comprising:
a patient table that comprises a lying surface for a person,
a robotic arm having a plurality of links and a plurality of joints arranged alternately in series in a kinematic chain of the robotic arm,
wherein the first link in the kinematic chain of the robotic arm forms a base frame for fastening the robotic arm on a support surface, and the last link in the kinematic chain of the robotic arm forms a mounting flange of the robotic arm to which the patient table is fastened,
and the robotic arm comprises at least one mechanical locking device which is designed to mechanically block one of the joints of the robotic arm by the mechanical locking device in the kinematic chain of the robotic arm mechanically connecting the link of the robotic arm immediately downstream of the joint to be blocked to a support component upstream of the joint in the kinematic chain of the robotic arm at a point remote from the joint to be blocked.

SUMMARY

The object of the invention is to improve a patient-positioning device in such a way that the patient table to be moved by the patient-positioning device can assume a low access height for patients and thus has a compact structure and nevertheless comprises a high degree of flexibility of movement.

The object is inventively achieved by a patient-positioning device, comprising:
a first link, which is designed as a base frame, for fastening the patient-positioning device on a support surface,
a second link which is mounted on the first link so as to be rotatable about a first axis of rotation by means of a first joint,
a third link which is mounted on the second link so as to be rotatable about a second axis of rotation by means of a second joint,
wherein the third link is arranged on the second link by means of the second joint in such a way that, with a floor mounting of the first link, the third link is arranged below the second link by means of the second joint, in order to suspend the third link on the second link in an overhead arrangement by means of the second joint, wherein the third link is mounted so as to be rotatable under the second link by means of the second joint, a fourth link which is mounted on the third link so as to be rotatable about a third axis of rotation by means of a third joint, a fifth link which is mounted on the fourth link so as to be rotatable about a fourth axis of rotation by means of a fourth joint, a sixth link which is mounted on the fifth link so as to be rotatable about a fifth axis of rotation by means of a fifth joint, and a seventh link, which is mounted on the sixth link so as to be rotatable about a sixth axis of rotation by means of a sixth joint, wherein the seventh link comprises a mounting flange on which a patient table of the patient-positioning device is arranged.

In this respect, the patient-positioning device can comprise a robotic arm which is designed to position the patient table in space. By repositioning the patient table by means of this robotic arm, a patient can be positioned particularly advantageously in space for medical treatment.

The patient-positioning device can accordingly be formed from links and joints which are strung together as a so-called linear kinematic chain. The links can, among other things, be bar-shaped, whether straight or curved, and, for example, have a rectangular, circular or oval cross section. The links can thus comprise a straight or a curved longitudinal extension. The links can in particular be formed from hollow bodies.

The base frame attaches the patient-positioning device to a support surface. The support surface can also be referred to as a base for the patient-positioning device. The support surface or the base can be the floor of a room. Alternatively, the support surface or the base can also be a movable sled of a linear axis, i.e. a carriage that can be moved on rails. The sled, which in this respect can be a carriage, is also referred to as a carriage, among other things. The base frame forms a link of the patient-positioning device. The support surface can represent a fastening surface on which the patient-positioning device is mounted. Indeed, the support surface can be the floor of a room. The support surface does not necessarily have to be the floor of a room. Rather, the support surface can be formed in special configurations and in special applications also by a side wall or even by a ceiling of a room.

Each axis of rotation can represent a degree of freedom of the kinematic chain of links and joints of the patient-positioning device. The axes of rotation are each assigned to a joint of the patient-positioning device. Each joint can be a swivel joint to the extent that a connected link can be rotated relative to an adjacent link.

With a floor mounting, the patient-positioning device can be fastened to the support surface, preferably in a horizontal plane, on the floor in a room of a building. The patient-positioning device can, however, optionally also be attached to the support surface at an angle, for example from 5 to 30 degrees, in a position and orientation of the support surface that is tilted from the horizontal plane.

An overhead arrangement of the third link to the second link means an arrangement of the third link below the second link by means of the second joint. The third link in this respect is mounted suspended from the second link. The third link is consequently mounted so as to be rotatable about the second axis of rotation under the second link of the patient-positioning device by means of the second joint.

The mounting flange connects the patient table to the kinematic chain of links and joints of the patient-positioning device, so that the patient table can be moved in space, in particular adjusted and/or rotated, by automatic adjustment of the links of the patient-positioning device. The mounting flange thus forms a distal end link of the links of the patient-positioning device.

In order to change the position and/or position and orientation of the patient table, the patient-positioning device can adjust the respective links of the patient-positioning device relative to one another by means of the respective joints and a control device that moves the joints. For this purpose, two directly adjacent links can be connected to one another in such a way that they can be adjusted by one of the joints. By means of the inventive overhead arrangement of the third link on the second link, the third link can be moved below the second link.

When the first link of the patient-positioning device is mounted on the support surface, in particular on the floor of a room, the first axis of rotation can determine the movement of the patient table in a first circular path about the first link. In addition, the second axis of rotation can determine the movement of the patient table in a second circular path about the second link. The third axis of rotation can in particular change the height of the patient table in relation to the support surface in such a way that a very low access height can also be assumed for the patient and a different treatment height can be assumed during the treatment of the patient. The fourth axis of rotation can define a roll angle of the patient table about its longitudinal axis, by which roll angle the patient table can be tilted. By means of the fifth axis of rotation, the patient table can be tilted in the longitudinal direction of the patient table, so that the patient table can be pitched in relation to its longitudinal axis. The sixth axis of rotation can rotate the patient table about the seventh link.

As a result of the overhead arrangement of the third link on the second link, the patient-positioning device can assume a low access height by the patient table being positionable closer to the floor due to the freedom provided by the overhead arrangement. Furthermore, a compact configuration of the joints and links can be achieved and, in addition to a large range, the patient table can also be positioned very close to the base frame.

The second link can be designed as a first carousel which is rotatably arranged on the first link by means of the first joint, wherein the third link is designed as a second carousel which is rotatably arranged on the second link by means of the second joint.

The first carousel and the second carousel each form a link of the patient-positioning device. The first carousel and the second carousel respectively form the first axis of rotation and the second axis of rotation of the patient-positioning device. By means of the first axis of rotation and the second axis of rotation, the second link and the third link of the patient-positioning device can each execute a rotary movement.

Due to the arrangement of the first carousel and the second carousel, in particular with vertical axes of rotation, the front arm of the patient-positioning device, which comprises the fourth axis of rotation, the fifth axis of rotation and the sixth axis of rotation, can be pivoted in a circular path at a constant height about a vertical pivot axis. The patient table with its lying surface preferably remains in a substantially horizontal plane.

By constructing the second link and the third link as a first carousel and a second carousel, the patient table can either be moved on a circular path or a circular arc at a short distance from the base frame of the patient-positioning device or be moved a further distance from the base frame of the patient-positioning device.

The first axis of rotation and the second axis of rotation can be arranged at least substantially parallel to one another, regardless of the rotational position of the second link about the first axis of rotation, in such a way that the second joint with its second axis of rotation always maintains its parallel orientation to the first axis of rotation, even when the rotational position of the second link about the first axis of rotation is changed.

The parallel arrangement of the first axis of rotation and the second axis of rotation has the effect that in the case of a vertically oriented first axis of rotation and second axis of rotation the patient table always remains with its lying surface in an essentially horizontal orientation, regardless of which specific rotational position the first joint and/or the second joint is assuming at the time. The angle of rotation of the first joint can be 360 degrees, depending on the particular situation, or, depending on the structural design, the first joint can even execute any number of complete revolutions. In a modified, more preferred embodiment, however, the angle of rotation can also be limited to a maximum angle of rotation of less than 360 degrees. The angle of rotation can thus preferably be on the order of magnitude of a maximum of 200 degrees to 250 degrees. In a special version, the maximum angle of rotation is 220 degrees. With this maximum angle of rotation of 220 degrees, starting from a zero position of the carousel, the angle of rotation can be plus 110 degrees in one direction of rotation and minus 110 degrees in the other direction of rotation. The maximum angle of rotation can be fixed mechanically both in one direction of rotation and in the other direction of rotation, for example by end stops. The end stops can optionally also be designed to be adjustable.

The first axis of rotation and the second axis of rotation can thus always be arranged at least substantially vertically, regardless of the rotational position of the second link about the first axis of rotation, in such a way that the second joint with its second axis of rotation always maintains its vertical orientation to the first axis of rotation, even when the rotational position of the second link about the first axis of rotation is changed.

Rotating the second link about the first axis of rotation and rotating the third link about the second axis of rotation can allow the third link to maintain its orientation in space. This is the case when the second joint is rotated with the same rotational velocity as the first joint, but with the opposite direction of rotation. By means of the rotation about the first axis of rotation and the rotation about the second axis of rotation parallel to the first axis of rotation, the radial distance of the seventh link, i.e. the mounting flange of the patient-positioning device, can be adjusted or varied.

This arrangement allows the patient-positioning device to precisely reach spatial points in close proximity to the base frame of the patient-positioning device by moving the second link about the first axis of rotation and the third link about the second axis of rotation. As a result, a compact structure can be achieved which at the same time allows a high degree of flexibility of movement.

The second axis of rotation and the third axis of rotation can be arranged at least substantially orthogonally to one another, regardless of the rotational position of the second link about the first axis of rotation and regardless of the rotational position of the third link about the second axis of rotation, such that the third joint with its third axis of rotation always maintains its orthogonal orientation to the first axis of rotation and to the second axis of rotation, even when the rotational position of the second link about the first axis of rotation is changed and even when the rotational position of the third link about the second axis of rotation is changed.

The second axis of rotation and the third axis of rotation can be arranged at least substantially at right angles, i.e. orthogonally to one another, regardless of the rotational position of the second link about the first axis of rotation and regardless of the rotational position of the third link about the second axis of rotation, such that the third joint with its third axis of rotation always maintains its horizontal orientation to the vertical first axis of rotation and to the vertical second axis of rotation, even when the rotational position of the second link about the first axis of rotation is changed and even when the rotational position of the third link about the second axis of rotation is changed.

Rotating the fourth link about the third axis of rotation can change the distance, i.e. the height, of the seventh link, from the support surface, in particular with the patient table supported on the seventh link. The fourth link thus forms a link arm, which can thus be pivoted in particular about a horizontal third axis of rotation, as a result of which the height of the patient table relative to the support surface, in particular relative to a floor of a room, can be reduced or increased.

By means of the orthogonal arrangement of the third axis of rotation to the second axis of rotation, the access height for patients on the patient table can be adjusted and/or the patient table can be brought into a required distance from the support surface or from a medical device.

The patient-positioning device can comprise at least one motor with a motor shaft and a gear unit with a gear input shaft, wherein the motor shaft is connected to the gear input shaft to drive the gear unit, and the gear input shaft and/or a gear output shaft of the gear unit is arranged parallel to the second axis of rotation in the second joint, and the motor is arranged on the second link in such a way that the motor shaft is arranged parallel to the gear input shaft and/or the gear output shaft of the gear unit and parallel to the second axis of rotation above the second joint, wherein the motor transmits a torque to the gear unit.

The patient-positioning device can comprise motors, in particular electric motors, which allow movement of the patient-positioning device by direct or at least indirect control of an electronic control device. The motors can comprise motor shafts which are able to transmit a suitable torque to the associated joints of the patient-positioning device.

The gear unit in question can in particular serve to form a drive support and/or to implement a gear ratio. For this purpose, the gear unit can optionally comprise a gear input shaft and a gear output shaft in addition to other shafts. The gear input shaft introduces a torque into the gear unit which the gear unit converts, for example, into a greater torque and is output via the gear output shaft or a gear output flange.

The motor in question can be designed to control an assigned joint of the patient-positioning device. The patient-positioning device can comprise one, two or more motors. In each case one motor can in particular control exactly one associated joint of the patient-positioning device. At least one motor of the motors can be arranged on the second joint in such a way that the motor shaft of this motor is positioned parallel to the gear input shaft of the second joint. By means of this positioning of the at least one motor and of the gear unit, the torque of the motor can in particular be transmitted directly.

By arranging the motor shaft and the gear input shaft in parallel, a compact design of the links and joints can be achieved, in which the motor shaft and the gear input shaft can be close to one another. As a result, the patient-positioning device can comprise greater freedom of movement and/or a more compact design.

The patient-positioning device can comprise at least one motor having a motor shaft and a gear unit with a gear input shaft, wherein the motor shaft is connected to the gear input shaft to drive the gear unit, and the gear input shaft and/or a gear output shaft of the gear unit is arranged parallel to the second axis of rotation in the second joint, and the motor is arranged on the second link in such a way that the motor shaft is arranged orthogonally to the gear input shaft and/or the gear output shaft of the gear unit and orthogonally to the second axis of rotation on the second joint, wherein the motor transmits a torque to the gear input shaft of the gear unit via an angular gear. In a first variant, the motor shaft and the gear input shaft can be arranged parallel to one another, as described above, or even be arranged coaxially to one another. In terms of the type of arrangement, a type of series connection is implemented. However, due to the large gear diameter and the significant axial motor length, this structure can take up a lot of space. In order to shorten the construction length or the construction height, the motor can be rotated by 90 degrees relative to its previous axis of rotation and the axis of the gear input shaft in a modified design variant of the arrangement of the motor shaft relative to the gear input shaft. In order to be able to transfer the motor drive torque to the main gear unit, an additional intermediate gear stage, such as the described angular gear unit, can be used. The object of such an angular gear is thus primarily to redirect the drive torque by 90 degrees, because the axes of rotation of the motor shaft and the gear input shaft are rotated by 90 degrees relative to each other. The secondary object of the angular gear can be to increase the torque. Thus, the angular gear can have different gear ratios.

A compact design of the links and joints can be achieved through an orthogonal, i.e. right-angled arrangement of the motor shaft and gear input shaft. As a result, the patient-positioning device can comprise greater freedom of movement and/or a more compact design.

The gear unit can be designed as a hollow shaft gear unit for transmitting a torque of the motor, wherein at least the gear output shaft and/or the gear input shaft of the gear unit is designed as a hollow shaft.

The gear unit can be designed as a hollow shaft gear unit, so that power supply lines can be routed through the hollow shaft gear unit via the joint assigned to the hollow shaft gear unit.

The hollow shaft gear unit can be designed to convert torques, directions of rotation and/or speeds. The hollow shaft gear unit can be designed to receive an input rotary movement by means of a gear input shaft and to convert this input rotary movement. The converted input rotary movement can be output as an output rotary movement by means of a gear output shaft.

By means of the hollow shaft gear unit, a more compact design can be combined with more efficient cable routing in such a way that cables or lines can be routed more directly and the freedom of movement of the patient-positioning device is not restricted.

The patient-positioning device can comprise at least one power supply line for electrically controlling at least one motor of the patient-positioning device, which line is guided from the base frame of the patient-positioning device to the second joint via a cavity in the second link, is further routed by means of a central passage in the hollow shaft gear unit of the second joint to an outlet opening of the second link and, starting from the outlet opening, is guided out of the second link and is passed outside the third link and is guided into the fourth joint via an entry opening.

The power supply line can supply at least one motor of the patient-positioning device with electrical power and/or control signals. Accordingly, the motors of the patient-positioning device can be controlled by a control device via the power supply line.

The power supply line can be designed to transmit signals and electrical power from the control device to the motors of the patient-positioning device via the kinematics of the links and joints of the patient-positioning device. At least one unidirectional or also bidirectional transmission of control signals and/or power can take place. At least one motor of the patient-positioning device, a plurality of motors of the patient-positioning device or all motors of the patient-positioning device can be connected to the control device via the power supply line, so that these motors can be supplied with electrical power and/or control signals.

By controlling the at least one motor of the patient-positioning device or, for example, all of the motors of the patient-positioning device via the at least partially internal power supply line, a compact design of the patient-positioning device can be achieved.

The power supply line can comprise at least one first loop, which is designed to compensate the length of the power supply line during a rotary movement about the first axis of rotation, wherein the first loop is guided coaxially around the first joint.

A loop can be understood to mean an excess length of the power supply line, so that the entire length of the power supply line is longer than the minimum length of the power supply line for connecting the components that are connected. The loop or the excess length of the power supply line forms a reservoir of length, so that the reserve length of the power supply line can be used in various configuration positions of the joints of the patient-positioning device in order to be able to track the respective movement of the joints. In the case of the first loop, this reserve length can be placed around the first joint.

When at least one of the axes or the joints of the patient-positioning device is moved, the loop can provide the additionally required length of the power supply line, so that tearing of the power supply line and/or excessive wear and tear can be prevented during the movement of the joints of the patient-positioning device.

The axial arrangement of the at least one loop around a joint of the patient-positioning device represents a compact variant for maintaining a line reserve for the power supply line, with which smooth operation of the patient-positioning device can be ensured.

The power supply line can comprise at least one second loop, which is designed to compensate the length of the power supply line during a rotary movement about the second axis of rotation and/or the third axis of rotation, wherein the second loop is guided coaxially around the third joint.

The patient-positioning device can comprise a linear axis which has a linearly movable sled on which the base frame of the patient-positioning device can be arranged in order to position the patient-positioning device in a linearly adjustable manner.

The linear axis can movably position the patient-positioning device on its support surface. The linear axis is designed to move the patient-positioning device in particular in an at least substantially horizontal plane. The entire patient-positioning device can thus be moved relative to the floor in a room by means of the sled.

The patient-positioning device can be moved in its position in space by means of the movement of the sled of the linear axis.

With this additional axis in the form of the linear axis, the patient-positioning device can significantly expand its range of action, so that more distant positions in space can be reached.

The patient-positioning device can comprise a control device which is set up to drive at least one motor of the patient-positioning device, wherein at least one motor of the patient-positioning device adjusts the first joint, the second joint, the third joint, the fourth joint, the fifth joint and/or the sixth joint to reposition the patient table.

The control device can be designed as a computer or a microcomputer, for example. The control device can be configured to generate signals for controlling the motors of the patient-positioning device.

The object is also achieved by a medical work station comprising a medical device and a patient-positioning device according to one or more of the embodiments as described.

The inventive medical work station is provided in particular for radiation therapy or for diagnostics. The medical device can thus preferably be a device for generating ionizing, high-energy radiation, such as gamma radiation, X-rays, or even accelerated electrons, neutrons, protons or heavy ions. The device for generating ionizing, high-energy radiation comprises, for example, a radiation source which generates the ionizing, high-energy radiation.

Specific embodiments of the invention are explained in more detail in the following description with reference to the accompanying figures. Specific features of these exemplary embodiments can represent general features of the invention regardless of the specific context in which they are mentioned, possibly also considered individually or in further combinations.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

DETAILED DESCRIPTION

Figure 1:
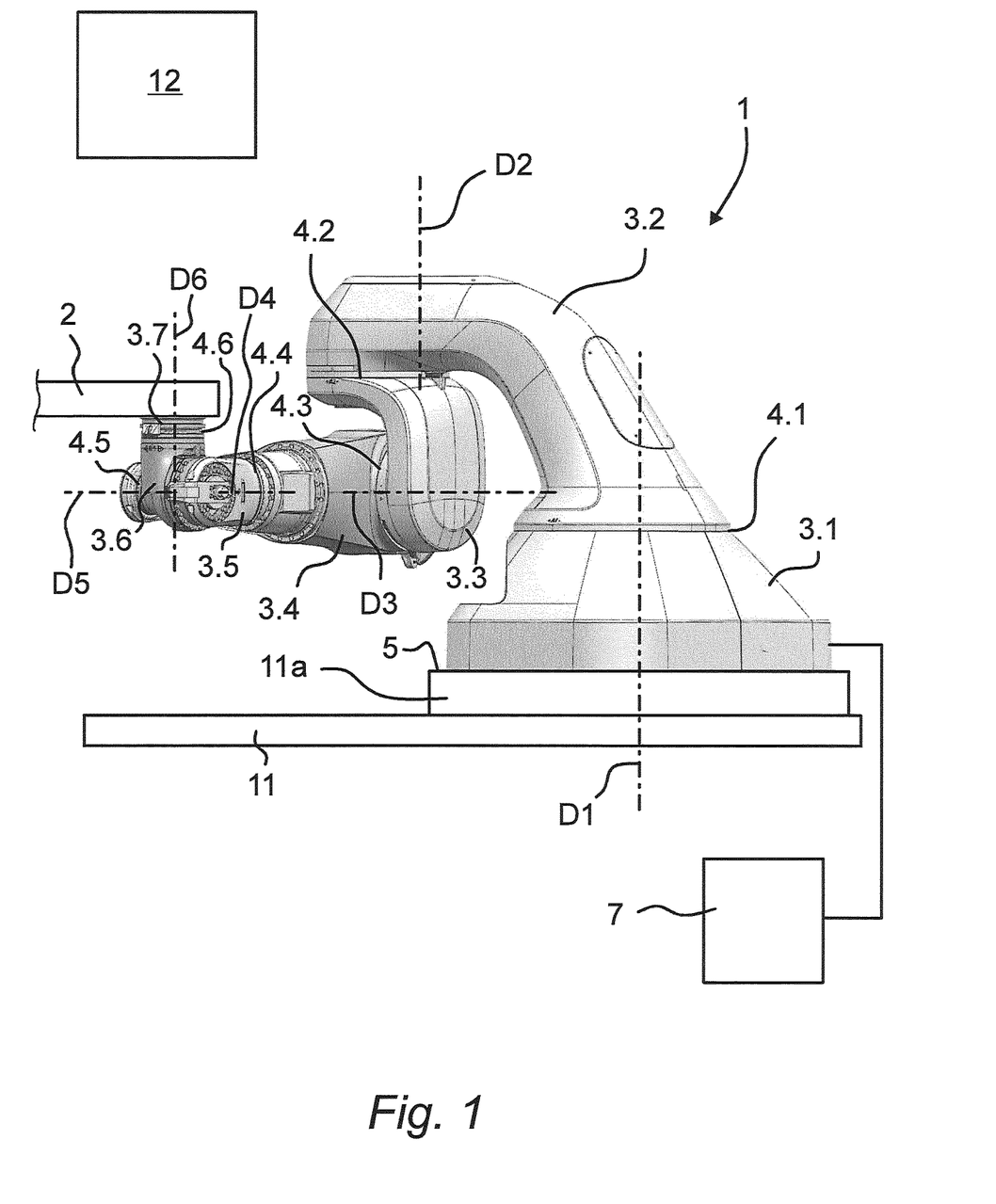
FIG. 1 is a schematic perspective illustration of a first embodiment of an inventive patient-positioning device.
Figure 2:
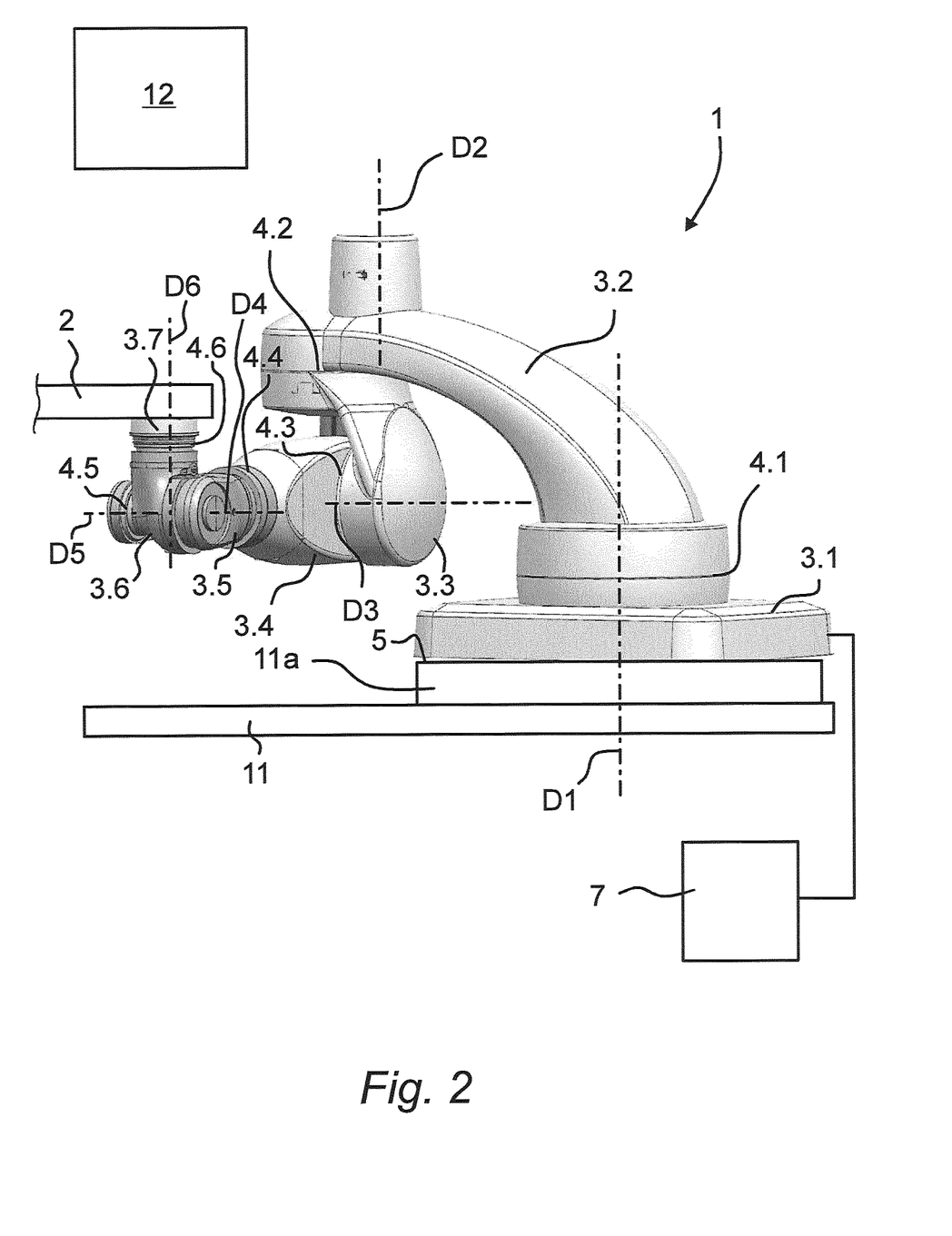
FIG. 2 is a schematic perspective illustration of a second embodiment of an inventive patient-positioning device.
Figure 3:
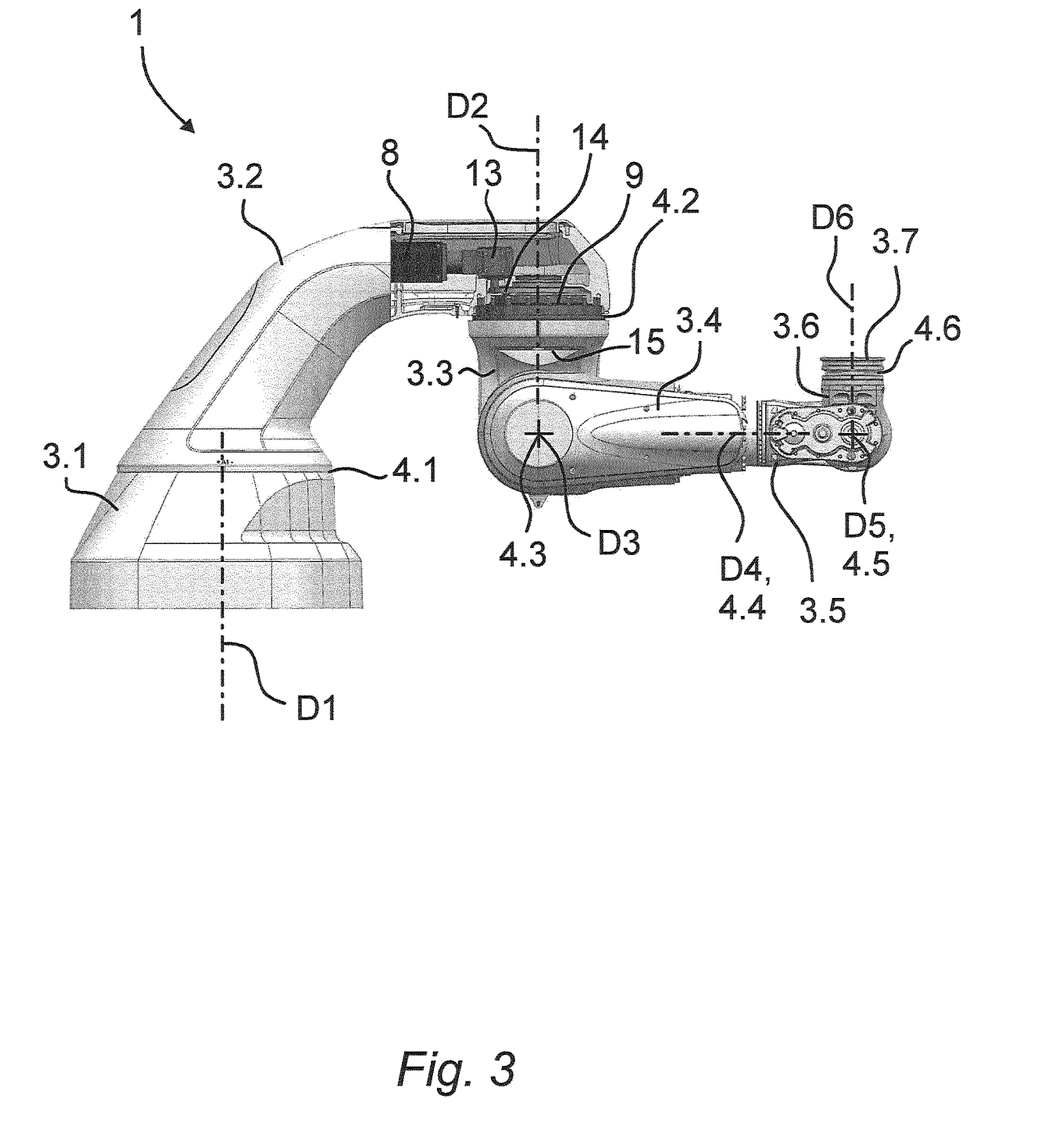
FIG. 3 is a schematic partial sectional view of the patient-positioning device according to the first embodiment according to FIG. 1 with a detailed view of the motor and the gear unit on the second joint.
Figure 4:
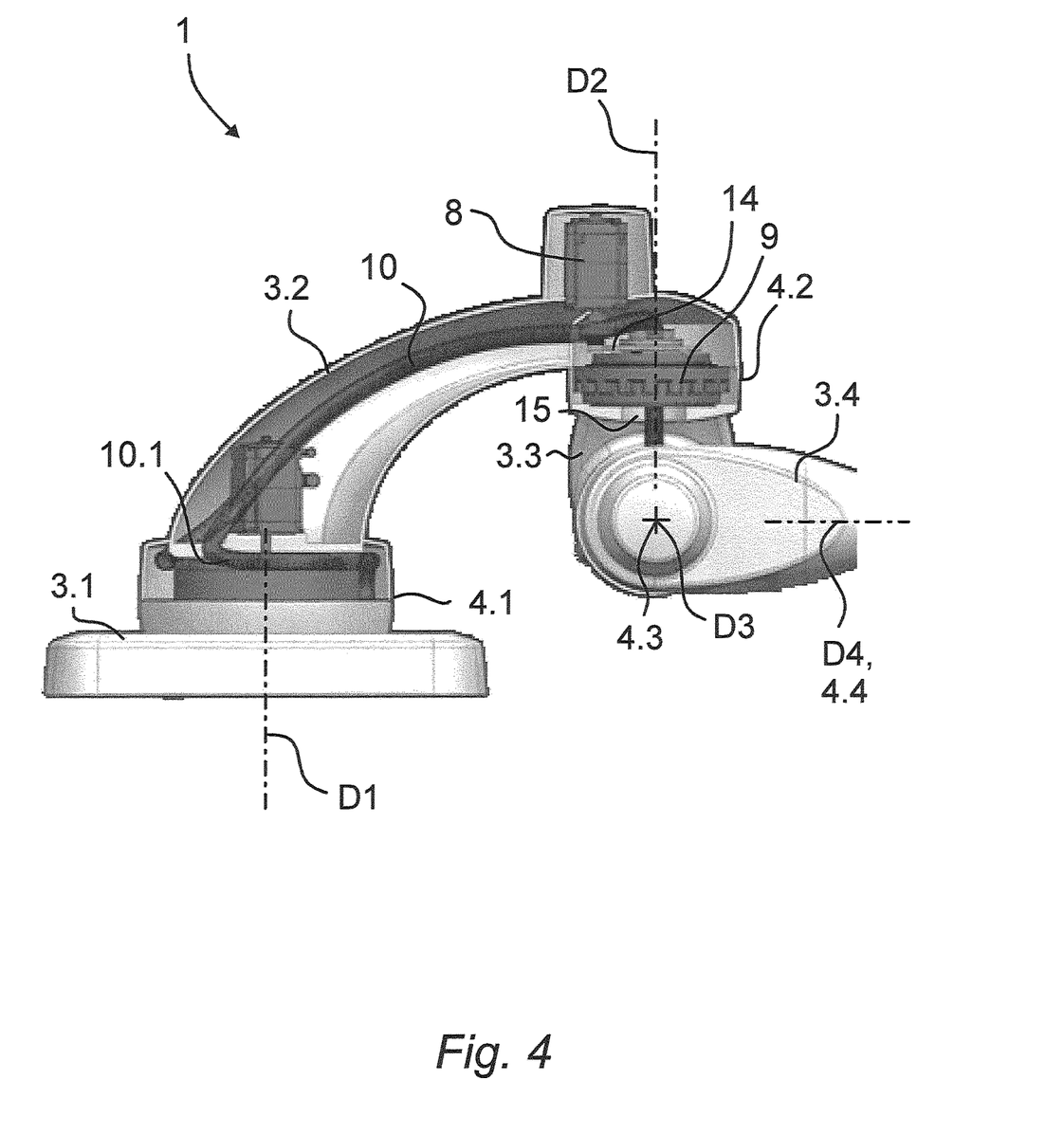
FIG. 4 is a schematic partial sectional view of the patient-positioning device according to the second embodiment according to FIG. 2 with a detailed view of the motor and the gear unit on the second joint, as well as a power supply line.

FIG. 1, FIG. 3 and FIG. 5 to FIG. 7 show an exemplary first embodiment of an inventive patient-positioning device 1. FIG. 2 and FIG. 4 show a modified second embodiment of an inventive patient-positioning device 1.

The first embodiment of the patient-positioning device 1 differs from the modified second embodiment of the patient-positioning device 1 essentially in the geometrical design of the second link 3.2 and the third link 3.3 as well as the arrangement of the motor 8 on the second link 3.2.

However, both embodiments of the patient-positioning device 1 have the following common features.

The patient-positioning device 1 comprises a first link 3.1, which is designed as a base frame for mounting to a support surface 5. In the case of the present embodiments, the first link 3.1 is mounted on a sled 11a of a linear axis 11.

To form a first axis of rotation D1, which in the present embodiments runs vertically due to floor mounting of the patient-positioning device 1, a second link 3.2 of the patient-positioning device 1 is rotatably mounted on the first link 3.1 by means of a first joint 4.1 of the patient-positioning device 1.

To form a second axis of rotation D2, which in the present embodiments also runs vertically due to a floor mounting of the patient-positioning device 1 and the shape of the second link 3.2, a third link 3.3 of the patient-positioning device 1 is rotatably mounted on the second link 3.2 by means of a second joint 4.2 of the patient-positioning device 1.

The arrangement of the third link 3.3 below the second link 3.2 is inventively implemented in such a way that the third link 3.3 is arranged suspended on the second link 3.2 in an overhead arrangement. The second link 3.2 extends completely over the second joint 4.2. In all of its rotational positions, the third link 3.3 is always below the free end portion of the second link, on which free end portion the second joint 4.2 is arranged or formed.

To form a third axis of rotation D3, which in the present embodiments extends horizontally due to a floor mounting of the patient-positioning device 1 and due to the shape of the second link 3.2 and the shape of the third link 3.3., a fourth link 3.4 of the patient-positioning device 1 can be rotated by means of a third joint 4.3 of the patient-positioning device 1, i.e., it is mounted so as to be rotatable about the horizontal axis of rotation D3 on the third link 3.3.

The third link 3.3 comprises an arcuate or inclined middle portion, which rigidly connects a proximal end portion of the third link 3.3, which comprises the second joint 4.2, to a distal end portion of the third link 3.3, which comprises the third joint 4.3, at a right angle in such a way that the horizontal third axis of rotation D3 is always aligned perpendicular to the vertical second axis of rotation D2.

To form a fourth axis of rotation D4, which runs in the longitudinal extension of the fourth link 3.4 and fifth link 3.5, the fifth link 3.5 of the patient-positioning device 1 is rotatably mounted on the fourth link 3.4 by means of a fourth joint 4.4 of the patient-positioning device 1.

The fourth joint 4.4, a fifth joint 4.5 and a sixth joint 4.6 of the patient-positioning device 1 are designed analogously to a known robotic hand of a kick arm robot with serial kinematics.

Accordingly, to form a fifth axis of rotation D5, which always extends perpendicular to the fourth axis of rotation D4, the sixth link 3.6 of the patient-positioning device 1 is rotatably mounted on the fifth link 3.5 by means of a fifth joint 4.5 of the patient-positioning device 1.

In addition, to form a sixth axis of rotation D6, which always extends perpendicular to the fifth axis of rotation D5, the seventh link 3.7 of the patient-positioning device 1 is rotatably mounted on the sixth link 3.6 by means of a sixth joint 4.6 of the patient-positioning device 1.

The seventh link 3.7 forms a mounting flange to which a patient table 2 of the patient-positioning device 1 is attached.

The second link 3.2 is designed as a first carousel and the third link 3.3 is designed as a second carousel.

The first axis of rotation D1 and the second axis of rotation D2 are always arranged at least substantially parallel to one another, regardless of the rotational position of the second link 3.2 about the first axis of rotation D1.

The second axis of rotation D2 and the third axis of rotation D3 are at least essentially always orthogonal to one another, regardless of the rotational position of the second link 3.2 about the first axis of rotation D1 and regardless of the rotational position of the third link 3.3 about the second axis of rotation D2.

The patient-positioning device 1 in question also comprises a control device 7 which is set up to control the motors of the patient-positioning device 1 in order to position the patient table 2 in space.

In the case of the present embodiments, the patient-positioning device 1 comprises the linear axis 11, which supports the first link 3.1 designed as a base frame so as to be movable.

The medical work station comprises the patient-positioning device 1 and a medical device 12. In the case of the present embodiments, the medical device 12 is a device known in principle to a person skilled in the art for generating ionizing, high-energy radiation, such as gamma radiation, X-rays, or even accelerated electrons, neutrons, protons or heavy ions. The device for generating ionizing, high-energy radiation comprises, for example, a radiation source which generates the ionizing, high-energy radiation.

In the first embodiment according to FIG. 1, FIG. 3 and FIG. 5 to FIG. 7, the motor 8, which drives the third link 3.3 via a gear unit 9 in the second link 3.2, has its motor shaft at a right angle to second axis of rotation D2 arranged in the second link 3.2. The motor 8 is coupled to the gear unit 9 by means of an angular gear 13. The angular gear 13 transmits the torque from the motor shaft to an output shaft of the angular gear 13. The output shaft of the angular gear 13 is coupled to a gear input shaft of the gear unit 9 via a torque-transmitting component arrangement 14. The output shaft of the angular gear 13 is arranged parallel to the gear input shaft 9.1 of the gear unit 9. The gear unit 9 is designed as a hollow shaft gear unit, i.e. at least the gear output shaft and/or the gear input shaft of the gear unit 9 are designed as a hollow shaft. With a floor mounting of the patient-positioning device 1 as shown, the motor shaft of the motor 8 is accordingly mounted in a horizontal orientation in the second link 3.2.

In the second embodiment according to FIG. 2 and FIG. 4, the motor 8, which drives the third link 3.3 via the gear unit 9 in the second link 3.2, is arranged with its motor shaft parallel to the second axis of rotation D2 in the second link 3.2. The motor 8 is coupled to the gear unit 9 by means of the torque-transmitting component arrangement 14. The component arrangement 14 transmits the torque from the motor shaft directly to the gear input shaft of the gear unit 9. The gear unit 9 is designed as a hollow shaft gear unit, i.e. at least the gear output shaft and/or the gear input shaft of the gear unit 8 are designed as a hollow shaft. With a floor mounting of the patient-positioning device 1 as shown, the motor shaft of the motor 8 is accordingly mounted in a vertical orientation in the second link 3.2.

FIG. 4 shows, in a (partial) sectional view of the second link 3.2 and the first link 3.1, a portion of a power supply line 10 on the patient-positioning device 1. The arrangement of the power supply line 10 shown in the case of the illustrated second embodiment can likewise also be implemented in the same way in the first embodiment.

The power supply line 10 is used to electrically control at least one motor of the patient-positioning device 1. The power supply line 10 is routed from the first link 3.1, i.e. from the base frame of the patient-positioning device 1, to the second joint 4.2 via a cavity in the second link 3.2, further routed by means of a central passage in the hollow shaft gear unit (gear unit 8) of the second joint 4.2 to an exit opening 15 of the second link 3.2 and, starting from the exit opening 15, routed out of the second link 3.2 and passed outside the third link 3.3 and introduced into the fourth joint 3.4 via an entry opening.

As can be seen in particular in FIG. 4, the power supply line 10 can comprise at least one first loop 10.1, which is designed to compensate the length of the power supply line 10 during a rotary movement about the first axis of rotation D1, wherein the first loop 10.1 is guided coaxially around the first joint 4.1.

The first loop 10.1 can provide the additionally required length of the power supply line 1 when at least one of the axes or the joints of the patient-positioning device 1 is moved, so that tearing of the power supply line 1 and/or excessive wear and tear can be prevented during the movement of the joints of the patient-positioning device 1.

Figure 5:
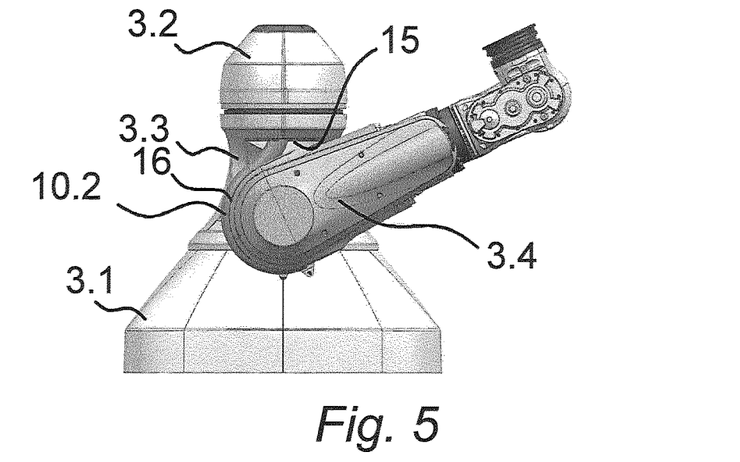
FIG. 5 is a perspective view of the patient-positioning device according to FIG. 1 with a front arm pivoted upward about the third axis of rotation.
Figure 6:
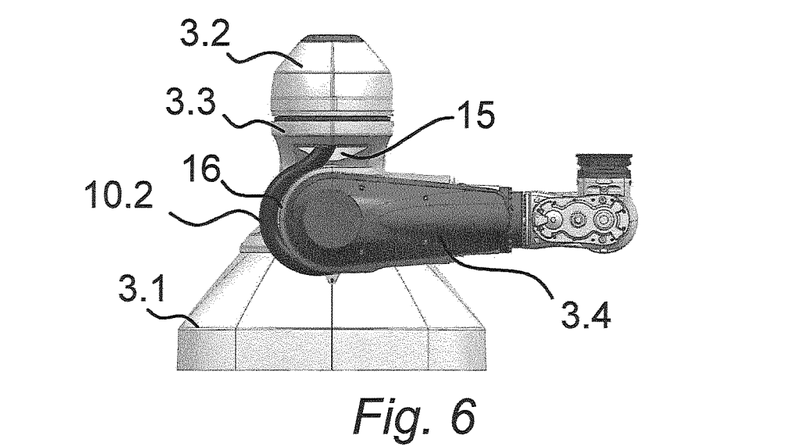
FIG. 6 is a perspective view of the patient-positioning device according to FIG. 1 with a front arm pivoted about the third axis of rotation into a horizontal position and orientation.
Figure 7:
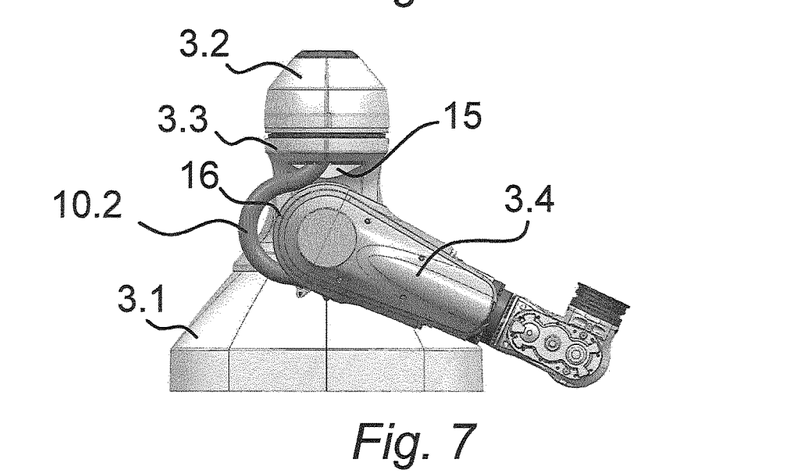
FIG. 7 is a perspective view of the patient-positioning device according to FIG. 1 with a front arm pivoted downward about the third axis of rotation.

As can be seen in particular in FIG. 5 to FIG. 7, the power supply line 10 can comprise at least one second loop 10.2, which is designed to compensate for the length of the power supply line 1 during a rotary movement about the second axis of rotation D2 and/or the third axis of rotation D3, wherein the second loop 10.2 is guided coaxially around the third joint 4.3.

FIG. 5 to FIG. 7 show the exemplary first embodiment of the patient device 1, each with different pivoting angle positions of the front arm of the patient-positioning device 1, in particular of the fourth link 3.4 about the third axis of rotation D3. FIG. 5 shows a swivel angle of −25 degrees, FIG. 6 shows a swivel angle of 0 degrees, and FIG. 7 shows a swivel angle of +25 degrees.

As shown in FIG. 5, the second loop 10.2 of the power supply line 10 is arranged in the pivoting angle position of −25 degrees flush with the channel-shaped guide 16 of the fourth link 3.4. In this flush position and orientation of the second loop 10.2 of the power supply line 10 with the channel-shaped guide 16 of the fourth link 3.4, the fourth link 3.4 is also in its maximum lifting position for the patient table 2.

As shown in FIG. 6, the second loop 10.2 of the power supply line 10 is arranged slightly raised from the channel-shaped guide 16 of the fourth link 3.4 in the pivoting angle position of 0 degrees.

As shown in FIG. 7, the second loop 10.2 of the power supply line 10 is arranged clearly raised from a channel-shaped guide 16 of the fourth link 3.4 in the pivoting angle position of FIG. 7 of +25 degrees. In this arrangement of FIG. 7, the fourth link 3.4 is in its maximum lowered position for the patient table 2.

While the present invention has been illustrated by a description of various embodiments, and while these embodiments have been described in considerable detail, it is not intended to restrict or in any way limit the scope of the appended claims to such de-tail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

What is claimed is:

1. A patient-positioning device, comprising:
    a first link configured as a base frame, and configured for fastening the patient-positioning device on a support surface;
    a second link mounted on the first link by a first joint so as to be rotatable about a first axis of rotation;
    a third link mounted on the second link by a second joint so as to be rotatable about a second axis of rotation;
    the second link having an angled or arcuate shape such that the first and second axes are parallel and spaced from one another;
    the third link having an angled or arcuate shape such that the second and third axes are perpendicular to one another;
    wherein the third link is arranged on the second link by the second joint in such a way that, with a floor mounting of the first link, the third link is arranged below the second link by the second joint in order to suspend the third link from the second link in an overhead arrangement of the second joint, whereby the third link is rotatably mounted by the second joint below the second link;
    a fourth link mounted on the third link by a third joint so as to be rotatable about a third axis of rotation;
    a fifth link mounted on the fourth link by a fourth joint so as to be rotatable about a fourth axis of rotation;
    a sixth link mounted on the fifth link by a fifth joint so as to be rotatable about a fifth axis of rotation; and
    a seventh link mounted on the sixth link by a sixth joint so as to be rotatable about a sixth axis of rotation;
    wherein the seventh link comprises a mounting flange on which a patient table of the patient-positioning device is arranged;
    whereby the arrangement of the second and third links facilitates positioning the patient table on the seventh link close to the floor to provide a low access height.

2. The patient-positioning device of claim 1, wherein:
    the second link is configured as a first carousel which is rotatably arranged on the first link by the first joint; and
    the third link is configured as a second carousel which is rotatably arranged on the second link by the second joint.

3. The patient-positioning device of claim 1, wherein the first axis of rotation and the second axis of rotation are arranged at least substantially parallel to one another regardless of the rotational position of the second link about the first axis of rotation, in such a way that the second joint with its second axis of rotation always maintains its parallel orientation to the first axis of rotation, even when the rotational position of the second link about the first axis of rotation changes.

4. The patient-positioning device of claim 1, wherein the second axis of rotation and the third axis of rotation, regardless of the rotational position of the second link about the first axis of rotation and regardless of the rotational position of the third link about the second axis of rotation, are arranged at least substantially orthogonally to one another in such a way that the third joint with its third axis of rotation always maintains its orthogonal orientation to the first axis of rotation and to the second axis of rotation, even when the rotational position of the second link about the first rotational axis changes and even when the rotational position of the third link about the second rotational axis changes.

5. The patient-positioning device of claim 1, further comprising:
    at least one motor comprising a motor shaft and a gear unit with a gear input shaft;
    wherein, for driving the gear unit:
        the motor shaft is connected to the gear input shaft,
        at least one of the gear input shaft or a gear output shaft of the gear unit is arranged parallel to the second axis of rotation in the second joint, and
        the motor is arranged on the second link in such a way that the motor shaft is arranged parallel to at least one of the gear input shaft or the gear output shaft of the gear unit, and is arranged parallel to the second axis of rotation above the second joint, wherein the motor transmits a torque to the gear unit.

6. The patient-positioning device of claim 5, wherein:
    the gear unit is configured as a hollow shaft gear unit for transmitting a torque of the motor; and
    at least one of the gear output shaft or the gear input shaft of the gear unit is configured as a hollow shaft.

7. The patient-positioning device of claim 1, further comprising:
    at least one motor comprising a motor shaft and a gear unit with a gear input shaft;
    wherein, for driving the gear unit:
        the motor shaft is connected to the gear input shaft,
        at least one of the gear input shaft or a gear output shaft of the gear unit is arranged parallel to the second axis of rotation in the second joint, and
        the motor is arranged on the second link in such a way that the motor shaft is arranged orthogonally to at least one of the gear input shaft or the gear output shaft of the gear unit, and is arranged orthogonally to the second axis of rotation on the second joint, wherein the motor transmits a torque to the gear input shaft of the gear unit via an angular gear.

8. The patient-positioning device of claim 7, wherein:
    the gear unit is configured as a hollow shaft gear unit for transmitting a torque of the motor; and
    at least one of the gear output shaft or the gear input shaft of the gear unit is configured as a hollow shaft.

9. The patient-positioning device of claim 1, further comprising:
    at least one motor for moving the patient-positioning device; and
    at least one power supply line for electrically controlling the at least one motor;
    wherein the at least one power supply line is routed from the base frame to the second joint, guided via a cavity in the second link, and is further routed via a central passage in a hollow shaft gear unit of the second joint to an outlet opening of the second link, and proceeding from the outlet opening is routed out of the second link and is routed outside the third link, and is routed into the fourth joint via an inlet opening.

10. The patient-positioning of claim 9, wherein the at least one power supply line comprises at least one first loop configured to compensate the length of the power supply line during a rotary movement about the first axis of rotation, wherein the first loop is guided coaxially around the first joint.

11. The patient-positioning device of claim 9, wherein the at least one power supply line comprises at least one second loop configured to compensate the length of the power supply line during a rotary movement about at least one of the second axis of rotation or the third axis of rotation, wherein the second loop is guided coaxially around the third axis of rotation.

12. The patient-positioning device of claim 1, further comprising:
- a linear axis which comprises a linearly movable, driven sled on which the base frame of the patient-positioning device is arranged in order to position the patient-positioning device in a linearly adjustable manner.

13. The patient-positioning device of claim 1, further comprising:
- a control device configured to drive at least one motor of the patient-positioning device;
- wherein at least one motor adjusts at least one of the first joint, the second joint, the third joint, the fourth joint, the fifth joint, or the sixth joint in order to reposition a patient table supported on the mounting flange of the seventh link.

14. A medical workstation, comprising: a patient-positioning device according to claim 1; and a medical device adapted for use with a patient supported on the patient-positioning device.

* * * * *